United States Patent
Zhang et al.

(10) Patent No.: US 7,754,891 B2
(45) Date of Patent: Jul. 13, 2010

(54) 5,5'-POSITION LINKED 1,1'-BIPHENYL AXIAL CHIRAL LIGAND AND METHOD FOR PREPARING THE SAME

(75) Inventors: Wanbin Zhang, Shanghai (CN); Yongjian Zhang, Shanghai (CN); Feijun Wang, Shanghai (CN)

(73) Assignee: Shanghai Jiaotong University, Shanghai (CN)

( * ) Notice: Subject to any disclaimer, the term of this patent is extended or adjusted under 35 U.S.C. 154(b) by 33 days.

(21) Appl. No.: 12/159,440

(22) PCT Filed: Dec. 29, 2006

(86) PCT No.: PCT/CN2006/003696
§ 371 (c)(1), (2), (4) Date: Oct. 9, 2008

(87) PCT Pub. No.: WO2007/073699
PCT Pub. Date: Jul. 5, 2007

(65) Prior Publication Data
US 2009/0156829 A1      Jun. 18, 2009

(30) Foreign Application Priority Data
Dec. 29, 2005   (CN) ........................ 2005 1 0112232
Dec. 29, 2005   (CN) ........................ 2005 1 0112233

(51) Int. Cl.
C07D 413/10      (2006.01)
(52) U.S. Cl. ...................................... 548/237; 548/238
(58) Field of Classification Search .................. 548/237, 548/238
See application file for complete search history.

(56) References Cited

U.S. PATENT DOCUMENTS

2004/0097738 A1     5/2004    Uozumi et al.

OTHER PUBLICATIONS

Gant T.G. et al, "The First Enantioselective Synthesis of the Chemotactic Factor Sirenin by an Intramolecular [2 + 1] Cyclization Using a New Chiral Catalyst", Tetrahedron Letters, vol. 36, No. 48, pp. 8745-8748 (1995).
Imai Y. et al., "Novel Chiral Bisoxazoline Ligands with a Biphenyl Backbone: Preparation, Complexation, and Application in Asymmetric Catalytic Reactions", J. Org. Chem., vol. 65, pp. 3326-3333 (2000).
Imai Y. et al., "Novel Axial Chiral Catalyst Derived from Biphenyl Ligand Bearing only Two ortho-Substituents", Tetrahedron Letters, vol. 38, No. 15, pp. 2681-2684 (1997).
Qlao Z. et al., "Progress of Chiral Bis(oxazoline)-Metal Complexes Utilized in Asymmetric Cyclopropanation", Chinese Journal of Organic Chemistry, vol. 24, No. 1, pp. 15-22 (2004).
Bian Q.-H. et al., "Progress in Synthesis of Chiral Bis(oxaline) Ligands", Chinese Journal of Organic Chemistry, vol. 24, No. 12, pp. 1542-1552 (2004).
U.S. Appl. No. 12/159,322 to Wanbin Zhang et al., filed Jun. 26, 2008.
Moorlag et al, "As Asymmetric Synthesis of a $C_2$ Symmetric Tetrasubstituted Biaryl: 2,2'-Dihydroxy-6,6'-Dimethyl-1,1'-Biphenyl, A Stable Chiral System," Tetrahedron Letters, vol. 34, No. 44, pp. 6993-6996, 1993.
Andrus et al., "Efficient Synthesis of 1,1'-Binaphthyl and 2,2'-Bi-o-tolyl-2,2'-bis(oxazoline)s and Preliminary Use of the Catalytic Asymmetric Allylic Oxidation of Cyclohexene," Journal of Organic Chemistry, vol. 62, No. 26, pp. 9365-9368, 1997.
Chemical Abstract 133:73820 for Imai et al., "Novel $C_2$-Symmetric Chiral Oxazolinylbiaryl Ligands Bearing a Hydroxyl Group," Synlett, No. 2, pp. 239-241, 2000.

*Primary Examiner*—Rebecca L Anderson
*Assistant Examiner*—Matthew P Coughlin
(74) *Attorney, Agent, or Firm*—Greenblum & Bernstein, P.L.C.

(57) ABSTRACT

The present invention relates to a 5,5'-position linked 1,1'-biphenyl axis chiral ligand in chemical industry field. The present invention incorporates both the central chirality of oxazoline and the axial chirality of diphenyls. Such ligand can be used in various asymmetric reactions catalyzed by metal with high reactivity and stereoselectivity, and thus represents a good application outlook. The ligand of the present invention has the formula of:

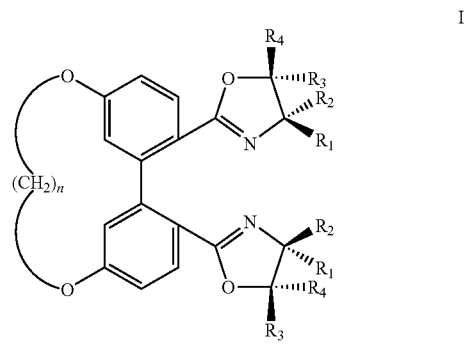

wherein: n=5, 6, 7, 8, 9, 10, 11 or 12; $R_1$=hydrogen, alkyl, substituted or unsubstituted aryl, substituted or unsubstituted benzyl; $R_2$=hydrogen, alkyl, substituted or unsubstituted aryl, substituted or unsubstituted benzyl; $R_3$=hydrogen, alkyl, substituted or unsubstituted aryl, substituted or unsubstituted benzyl; $R_4$=hydrogen, alkyl, substituted or unsubstituted aryl, substituted or unsubstituted benzyl.

13 Claims, No Drawings

5,5'-POSITION LINKED 1,1'-BIPHENYL AXIAL CHIRAL LIGAND AND METHOD FOR PREPARING THE SAME

TECHNICAL FIELD

The present invention relates to a compound in chemical industry field and its preparation method, more specifically, to 5,5'-position linked 1,1'-biphenyl axial chiral ligand and its preparation method.

BACKGROUND

The key point of asymmetric catalytic synthesis is how to design and synthesize chiral catalysts with high selectivity and catalytic activity, wherein chiral ligand is the source of asymmetric inducement and control produced by a catalyst. The $C_2$ type chiral bisoxazoline ligands have been widely applied in asymmetric reactions catalyzed by metals, such as asymmetric cyclopropylation reaction, intramolecular Wacker-Type cyclization reaction, asymmetric oxidation reaction of olefin, and intramolecular [2+1] ring addition reaction, and the like, due to their specific structures. During the past 30 years, a large numbers of chiral oxazoline ligands have been developed, especially those with various chiral side chains. Among others, axial chiral side chain has been widely used in the ligand due to its unique rigid structure. After years of studies, BINAP, an axial chiral ligand containing binaphthyl structure, has been applied successfully in industrially producing optical active compounds.

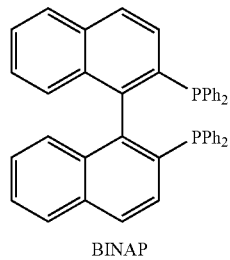

BINAP

The successful industrial application of BINAP, promotes the application of axial chirality in the design and synthesis of ligands. Oxazoline ligands containing axial chiral side chains have been developed successively and applied in various asymmetric reactions catalyzed by metals.

After searching in the prior art, E. J. Corey et. al. (*Tetrahedron Letters*, Vol. 36, No. 48, pp. 8745-8748, "The First Enantioselective Synthesis of the Chemotactic Factor Sirenin by an Intramolecular [2+1] Cyclization Using a New Chiral Catalyst") proposed a design concept of axial chiral ligand incorporating two relative large groups on the ortho position of biaryl axis. Although stable axial chirality can be obtained through their steric hindrance, the rotatable angle of biphenyl is also limited, i.e., the dihedral angle is limited. However, it has been confirmed that the dihedral angle influences the catalysis activity and selectivity of asymmetric catalytic reaction. Thus, design and synthesis of novel axial chiral ligand is among the most interesting research topics of organic chemistry.

SUMMARY OF THE INVENTION

The object of the present invention is to provide a 5,5'-position linked 1,1'-biphenyl axial chiral ligand and its preparation method, which differs from the current design concept for axial chiral ligand. It provides high reaction activity and stereo selectivity, as well as a broader range of dihedral angle. Therefore, the axial chiral ligands with better asymmetric catalytic effects can be screened out.

The present invention is carried out through the following technical solution. The 5,5'-position linked 1,1'-biphenyl axis chiral ligand (I) of the present invention has the following formula:

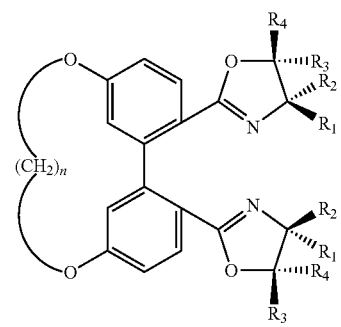

I wherein: n=5, 6, 7, 8, 9, 10, 11 or 12;

$R_1$=hydrogen, alkyl, substituted or unsubstituted aryl, substituted or unsubstituted benzyl;

$R_2$=hydrogen, alkyl, substituted or unsubstituted aryl, substituted or unsubstituted benzyl;

$R_3$=hydrogen, alkyl, substituted or unsubstituted aryl, substituted or unsubstituted benzyl;

$R_4$=hydrogen, alkyl, substituted aryl, substituted benzyl.

The alkyl group of $R_1$-$R_4$ in the formula is preferably $C_1$-$C_8$ straight or branched alkyl; the aryl group is preferably phenyl, p-tosyl, xylyl, or naphthoyl. In addition, above aryl and benzyl groups are optionally substituted by substitutes selected from alkyl, hydroxy, alkoxy, and halogen.

The ligand may be a diastereoisomeric compounds having a configuration of (R) or (S) at the axis, whose formulae are respectively as follows:

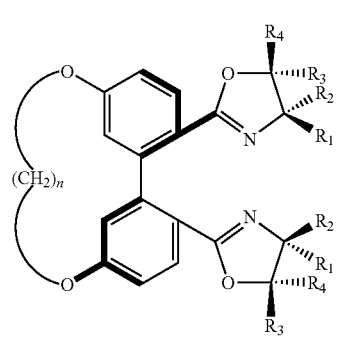

II

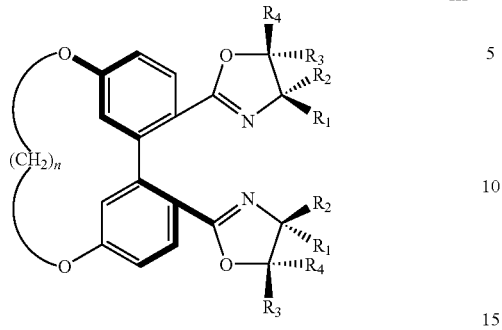

wherein n, $R_1$, $R_2$, $R_3$ and $R_4$ are defined as above.

The 5,5'-position linked 1,1'-biphenyl axial chiral ligand of the present invention can be synthesized by the method comprising: reacting the compound of formula (IX) with an activator that can activate the hydroxyl group selected from the group consisting of alkyl halosulfonium compound, aryl halosulfonium compound, phosphorus oxychloride, phosphoryl chloride, phosphorus pentachloride, thionyl chloride and triphenyl phosphine, in the presence of alkali(s) (described in details in the following step (7)). Further, the compound of formula (IX) is preferably those obtained by the following steps (1)-(6).

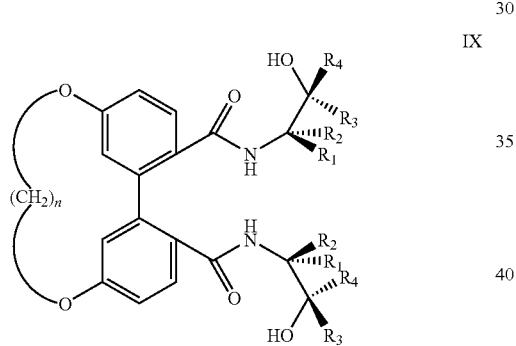

wherein n, $R_1$, $R_2$, $R_3$ and $R_4$ are defined as above.

In the method of the present invention, the formulae of compounds (IV)-(VII), as well as compounds (VIII) and (IX) having configurations of (R) and (S) at the axis are as follows:

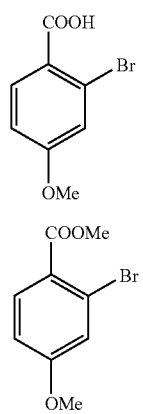

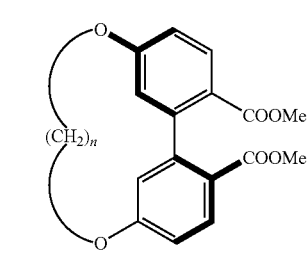

The formulae of compounds (VIII) and (IX) having a configuration of (R) at the axis are as follows:

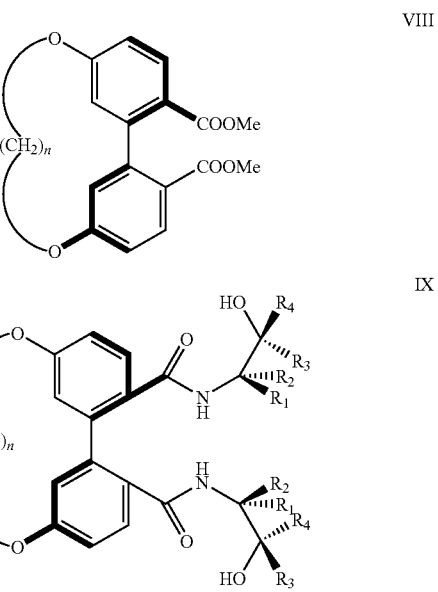

The formulae of compounds (VIII) and (IX) having a configuration of (S) at the axis are as follows:

-continued

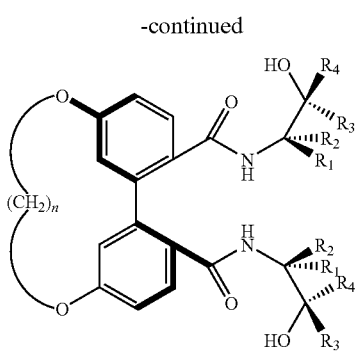

(IX)

In the above structures, n, $R_1$, $R_2$, $R_3$ and $R_4$ are defined as above.

Step (1): Synthesis of Compound (IV) from 2-bromo-4-methoxy Benzophenone

Bromine is added into aqueous sodium hydroxide, and then 2-bromo-4-methoxy benzophenone is added to give 2-bromo-4-methoxy benzoic acid (IV).

The reaction conditions are: the concentration of the aqueous sodium hydroxide is 5-20 wt %, the molar ratio of 2-bromo-4-methoxy benzophenone and bromine is 1:4-6, the reaction temperature is 20-70° C., and the reaction time is 12-20 hrs.

Step (2): Synthesis of Compound (V) from Compound (IV)

In an alcohol solvent such as methanol and the like, thionyl chloride is reacted with 2-bromo-4-methoxy benzoic acid (IV) to give methyl 2-bromo-4-methoxy benzoate.

The reaction conditions are: the molar ratio of compound (IV) and thionyl chloride is 1:1-10, the reaction temperature is 20-80° C., and the reaction time is 1-12 hrs.

Step (3): Synthesis of Compound (VI) from Compound (V)

Copper powder is contacted with compound (V) to give methyl 5,5'-dimethoxy-1,1'-biphenyl-2,2'-dicarboxylate (VI).

The reaction conditions are: the molar ratio of compound (V) and copper powder is 1:2-5, the reaction temperature is 150-180° C., and the reaction time is 2-24 hrs.

Step (4): Synthesis of Compound (VII) from Compound (VI)

To an organic solvent containing ethanethiol and aluminium trichloride, compound (VI) is added to give methyl 5,5'-dihydroxy-1,1'-biphenyl-2,2'-dicarboxylate (VII).

The reaction conditions are: the molar ratio of compound (VI) and aluminium trichloride is 1:3-6, the reaction temperature is 0-25° C., and the reaction time is 2-6 hrs.

The examples of the solvent are selected from the group consisting of esters, such as methyl formate, ethyl formate, methyl acetate, ethyl acetate, butyl acetate, ethyl propionate, and the like; halohydrocarbons, such as dichloromethane, trichloromethane, carbon tetrachloride, dichloroethane, dibromoethane, chlorobenzene, and the like; ethers, such as diethyl ether, dibutyl ether, 1,4-dioxane, tetrahydrofuran, and the like; carbonitriles, such as acetonitrile, butyronitrile, and the like; hydrocarbons, such as pentane, hexane, cyclohexane, and the like; etc. The solvent may be used alone, or two or more solvents may be used in combination.

Step (5): Synthesis of Compound (VIII) Having Configurations of (R) and (S) from Compound (VII)

In organic solvent(s), compound (VII) is reacted with dihalo alkane in the presence of alkali(s) to prepare 5,5'-linked methyl 5,5'-alkyldioxy-1,1'-biphenyl-2,2'-dicarboxylate (VIII) having mixed configurations of (R) and (S).

The reaction conditions are: the molar ratio of methyl 5,5'-dihydroxy-1,1'-biphenyl-2,2'-dicarboxylate and dihalo alkane is 1:1-1.5, the reaction temperature is 20-100° C., and the reaction time is 8-72 hrs. The organic solvents may be dimethyl formamide, acetonitrile, acetone, or the like.

The dihalo alkane is

wherein m=3, 4, 5, 6, 7, 8, 9 or 10; X and X' are chloride, bromide or iodide group, and may be same or different.

The alkali is not particularly limited. The examples of alkali include, but are not limited to, metal hydrides, such as sodium hydride, and the like; amines, such as trimethylamine, triethylamine, diisopropyl ethylamine, and the like; alkali hydroxides, such as potassium hydroxide, sodium hydroxide, and the like; alkali carbonates, such as sodium carbonate, potassium carbonate, and the like; alkoxides, such as sodium methoxide, potassium methoxide, sodium ethoxide, potassium ethoxide, and the like; piperidine; pyridine; potassium cresol; lithium alkylide; 1,8-diazobicyclo[5,4,0]hendec-7-ene; lithium bis(trimethylsilyl)amide; etc. The alkali may be used alone, or two or more alkalis may be used in combination.

Step (6): Synthesis of Compound (IX) Having a Configuration (R) or (S) from Compound (VIII) Having a Configuration of (R) or (S)

In an alcohol solvent such as methanol or the like, the mixtures of (VIII) having configurations of (R) and (S) is reacted with chiral amino alcohol in the present of alkali(s), to give amide diastereosiomeric compound (IX) having configurations of (R) and (S), respectively, at the axis.

The reaction conditions are: the molar ratio of compound (VIII) and chiral amino alcohol is 1:3-10, the reaction temperature is 50-120° C., and the reaction time is 4-12 hrs.

The amino alcohol is

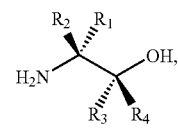

wherein $R_1$, $R_2$, $R_3$, $R_4$ are defined as above.

The alkali is not particularly limited. The examples of alkali include, but are not limited to, metal hydrides, such as sodium hydride, and the like; amines, such as trimethylamine, triethylamine, diisopropyl ethylamine, and the like; alkali hydroxides, such as potassium hydroxide, sodium hydroxide, and the like; alkali carbonates, such as sodium carbonate, potassium carbonate, and the like; alkoxides, such as sodium methoxide, potassium methoxide, sodium ethoxide, potassium ethoxide, and the like; piperidine; pyridine; potassium cresol; lithium alkylide; 1,8-diazobicyclo[5,4,0]hendec-7-ene; lithium bis(trimethylsilyl)amide; etc. The alkali may be used alone, or two or more alkalis may be used in combination.

Step (7): Synthesis of Compounds (II) and (III) Having a Configuration of (R) or (S) from Compound (IX) having a Configuration of (R) or (S)

In organic solvent(s), compound (IX) is reacted with an activator that can activate the hydroxyl group selected from the group consisting of alkyl halosulfonium compound, aryl halosulfonium compound, phosphorus oxychloride, phosphoryl chloride, phosphorus pentachloride, thionyl chloride and triphenyl phosphine, in the presence of alkali(s).

The reaction conditions are: the molar ratio of compound (IX), alkali and activator is 1:5-25:3-12, the reaction temperature is the room temperature, and the reaction time is 13-36 hrs.

The alkali is not particularly limited. The examples of alkali include, but are not limited to, metal hydrides, such as sodium hydride, and the like; amines, such as trimethylamine, triethylamine, diisopropyl ethylamine, and the like; alkali hydroxides, such as potassium hydroxide, sodium hydroxide, and the like; alkali carbonates, such as sodium carbonate, potassium carbonate, and the like; alkoxides, such as sodium methoxide, potassium methoxide, sodium ethoxide, potassium ethoxide, and the like; piperidine; pyridine; potassium cresol; lithium alkylide; 1,8-diazobicyclo[5,4,0]hendec-7-ene; lithium bis(trimethylsilyl)amide; etc. The alkali may be used alone, or two or more alkalis may be used in combination.

Further, the examples of the activator are alkyl halosulfonium compounds, such as methane sulfonyl chloride, and the like; aryl halosulfonium compounds, such as benzene sulfonyl chloride, p-toluene sulfonyl chloride, and the like; phosphoryl chloride; phosphorus pentachloride; thionyl chloride; or triphenyl phosphine.

The examples of the organic solvent are dichloromethane, trichloromethane, carbon tetrachloride, benzene, chlorobenzene, ethyl acetate, ethyl formate, dichloroethane, ethoxy acetic acid, and the like. The organic solvent may be used alone, or two or more organic solvents may be used in combination.

The present invention incorporates both the central chirality of oxazoline and the axial chirality of diphenyls. Such ligand can be used in various asymmetric reactions catalyzed by metal, such as asymmetric cyclopropylation reaction, intramolecular Wacker-Type cyclization reaction, asymmetric oxidation reaction of olefin, and intramolecular [2+1] ring addition reaction, and the like, with high reactivity and stereo selectivity, and thus represents a good application outlook.

In addition, the 5,5'-position linked 1,1'-biphenyl axis chiral ligand of the present invention can use simultaneously substances having configurations of (R) and (S), or can use substances having a single configuration of (R) or (S) separated through optical isolation using column chromatograph.

EMBODIMENTS OF THE INVENTION

The following examples are provided for illustration of the present invention, rather than the limitation of the present invention.

(1) Synthesis of Compound (IV) from 2-bromo-4-methoxy Benzophenone

In an ice bath, bromine (2.8 mL, 35.1 mmol) is slowly added dropwise into an aqueous NaOH (4.5 g, 111.4 mmol) solution (10 mL) and stirred for 10 mins. Then 2-bromo-4-methoxy benzophenone (2.1 g, 9.2 mmol) is added dropwise into the reaction, and stirred for 15 hrs at the temperature. After completion of the reaction, aqueous sodium sulfite is added to eliminate the unreacted sodium hypobromite. The resultant mixture is extracted with ethyl acetate to isolate neutral compound. The aqueous phase is then acidified with 6N HCl in an ice bath to give large quantities of white solid. The resultant is filtered under vacuum to give white solid (IV) (2.0 g, 95%).

$^1$H NMR (CDCl$_3$, 300 MHz) 8.05 (d, J=8.7 Hz, 1H, Ar—H), 7.23 (d, J=2.7 Hz, 1H, Ar—H), 6.91 (dd, J=8.7, 2.7 Hz, 1H, Ar—H), 3.87 (s, 3H, OCH$_3$).

(2) Synthesis of Compound (V) from Compound (IV)

In an ice bath, thionyl chloride (2.9 mL, 38.7 mmol) is slowly added dropwise into a solution of 2-bromo-4-methoxy benzoic acid (IV) (4.5 g, 19.3 mmol) in methanol (10 mL). Then the temperature of the mixture is allowed to reach the room temperature. The reaction mixture is then heated in reflux while reaction is monitored by TLC. The reaction is completed after 2 hrs. Excess thionyl chloride and methanol are evaporated. The residue is diluted with ethyl acetate, and is washed with water and then with saturated aqueous sodium carbonate. The organic phase is dried over anhydrous magnesium sulfate to give the product (V) (4.3 g, 91%).

$^1$H NMR (CDCl$_3$, 400 MHz) 7.87 (d, J=9.2 Hz, 1H, Ar—H), 7.19 (d, J=2.0 Hz, 1H, Ar—H), 6.87 (dd, J=9.2, 2.0 Hz, 1H, Ar—H), 3.90 (s, 3H, OCH$_3$), 3.84 (s, 3H, OCH$_3$).

(3) Synthesis of Compound (VI) from Compound (V)

The mixture of methyl 2-bromo-4-methoxy benzoate (V) (7.3 g, 29.6 mmol) and activated copper powder (7.0 g, 0.1 mol) is heated to 160-170° C. and stirred for 15 hrs under nitrogen. After cooling down, ethyl acetate is added. After filtration, the copper powder is washed with hot dichloromethane. The solvent is evaporated. The residue is recrystallized in ethyl acetate and petroleum ether to give product (VI) (3.0 g, 61%).

$^1$H NMR (CDCl$_3$, 400 MHz) 8.02 (d, J=8.8 Hz, 2H, Ar—H), 6.92 (dd, J=8.8, 2.8 Hz, 2H, Ar—H), 6.69 (d, J=2.8 Hz, 2H, Ar—H), 3.85 (s, 6H, OCH$_3$), 3.61 (s, 6H, OCH$_3$).

(4) Synthesis of Compound (VII) from Compound (VI)

In an ice bath, 3 mL ethanethiol is added dropwise into the solution of aluminium trichloride (0.8 g, 6.0 mmol) in 3 mL dichloromethane, and is dissolved while stirring. In the ice bath, the solution of compound (VI) (0.3 g, 1.0 mmol) in 5 mL dichloromethane is added dropwise into the above solution. The mixture is reacted at 0° C. for 2 hrs, and then reacted at the room temperature for 0.5 hr. The reaction is quenched with ice water and extracted with ethyl acetate. The resultant is dried over anhydrous magnesium sulfate. The solvent is evaporated. The residue is purified by column chromatography using petroleum ether and ethyl acetate as the eluent to give the target product (VII) (0.1 g, 33%).

$^1$H NMR (CD$_3$COCD$_3$, 400 MHz) 7.87 (d, J=8.8 Hz, 2H, Ar—H), 6.88 (dd, J=8.8, 2.4 Hz, 2H, Ar—H), 6.64 (d, 2H, J=2.4 Hz, Ar—H), 3.52 (s, 6H, OCH$_3$).

(5) Synthesis of Compound (VIII) from Compound (VII)

Compound (VII) (1.0 g, 3.3 mmol), anhydrous potassium carbonate (1.4 g, 9.9 mmol) and 1,8-dibromooctane (0.6 mL, 3.3 mmol) are added into 200 mL DMF. The resultant solution is stirred at room temperature for 7 hrs. The reaction solution is filtered and DMF is evaporated under vacuum. The residue is purified by column chromatography using ethyl acetate and petroleum ether as the eluent to give product (VIII) (0.8 g, 55%).

$^1$H NMR (CDCl$_3$, 400 MHz) 7.94 (d, J=8.4 Hz, 2H, Ar—H), 6.91 (dd, J=8.4, 2.4 Hz, 2H, Ar—H), 6.76 (d, J=2.4 Hz, 2H, Ar—H), 4.40 (t, J=7.6 Hz, 2H, OCH), 4.37 (t, J=7.6 Hz, 2H, OCH), 3.62 (s, 6H, OCH$_3$), 1.89-2.01 (m, 2H, CH$_2$), 1.55-1.67 (m, 2H, CH$_2$), 1.20-1.53 (m, 8H, CH$_2$).

(6) Synthesis of Compound (IX) from Compound (VIII) (R$_1$=i-Pr, R$_2$=R$_3$=R$_4$=H)

Compound (VIII) (0.3 g, 0.7 mmol), anhydrous potassium carbonate (0.4 g, 2.9 mmol), L-valinol (0.7 mL, 6.5 mmol) and 2 mL methanol are added into a 5 mL two neck flask, and are heated to 50° C. The reaction is monitored by TLC. After completion of the reaction, the resultant mixture is diluted with dichloromethane. The organic phase is washed with water and dried over anhydrous magnesium sulfate. The solvent is evaporated to give product (IX) (0.24 g, 60%).

(7) Synthesis of Compounds (II) and (III) from Compound (IX) ($R_1$=i-Pr, $R_2$=$R_3$=$R_4$=H)

The above crude product (IX) (0.16 g, 0.3 mmol) is dissolved in 10 mL dichloromethane, into which triethylamine (1.0 mL, 7.2 mmol) is added. In an ice bath, methyl sulfonyl chloride (0.3 mL, 3.4 mmol) is added and the mixture is reacted at r.t. for 18 hrs. TLC shows no change. The reaction mixture is diluted with dichloromethane, and is washed with water and saturated brine. Then the resultant is dried over anhydrous magnesium sulfate and the solvent is evaporated. The residue is purified by column chromatography using ethyl acetate and petroleum ether as the eluent to give two target products (II) (15.1 mg) and (III) (45.5 mg).

II: $^1$H NMR (CDCl$_3$, 400 MHz) 7.76 (s, J=8.4 Hz, 2H, Ar—H), 6.86 (dd, J=8.4, 2.4 Hz, 2H, Ar—H), 6.83 (d, J=2.4 Hz, 2H, Ar—H), 4.40 (t, J=7.6 Hz, 2H, OCH), 4.37 (t, J=7.6 Hz, 2H, OCH), 4.03-4.15 (m, 4H, OCH and NCH), 3.65-3.75 (m, 4H, OCH$_2$), 1.87-1.97 (m, 4H, CH), 1.55-1.68 (m, 4H, CH), 1.43-1.54 (m, 2H, CH), 1.37 (m, 4H, CH$_2$), 1.20-1.32 (m, 2H, CH), 0.93 (d, J=6.8 Hz, 6H, CH$_3$), 0.79 (d, J=6.8 Hz, 6H, CH$_3$).

III: $^1$H NMR (CDCl$_3$, 400 MHz) 7.71 (s, 2H, Ar—H), 6.85-6.93 (m, 4H, Ar—H), 4.43 (t, J=7.6 Hz, 2H, OCH), 4.30 (t, J=7.6 Hz, 2H, OCH), 4.03-4.20 (m, 4H, OCH and NCH), 3.75-3.90 (m, 4H, OCH$_2$), 1.90-2.01 (m, 2H, CH$_2$), 1.48-1.80 (m, 6H, CH), 1.42 (m, 4H, CH$_2$), 1.20-1.35 (m, 2H, CH), 0.81 (d, J=6.8 Hz, 6H, CH$_3$), 0.80 (d, J=6.8 Hz, 6H, CH$_3$).

The synthesis method of the Example is simple and provides high yield. The step 5 can provide effect synthesis method for other macro cyclic compounds. The result axis chiral ligand may coordinate with metal ions, such as copper, palladium and the like, to catalyze such reactions as asymmetric cyclopropylation reaction, intramolecular Wacker-Type cyclization reaction, asymmetric oxidation reaction of olefin, and intramolecular [2+1] ring addition reaction, and the like.

The invention claimed is:

1. A 5,5'-position linked 1,1'-biphenyl axial chiral ligand, characterized in that,
said ligand has the formula of:

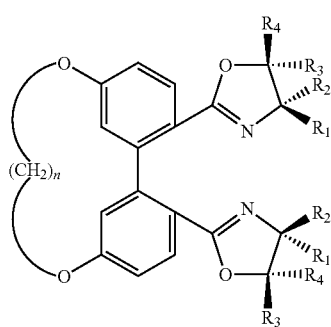

I wherein: n=5, 6, 7, 8, 9, 10, 11 or 12;
$R_1$=hydrogen, alkyl, substituted or unsubstituted aryl, substituted or unsubstituted benzyl;
$R_2$=hydrogen, alkyl, substituted or unsubstituted aryl, substituted or unsubstituted benzyl;
$R_3$=hydrogen, alkyl, substituted or unsubstituted aryl, substituted or unsubstituted benzyl;
$R_4$=hydrogen, alkyl, substituted or unsubstituted aryl, substituted or unsubstituted benzyl.

2. The 5,5'-position linked 1,1'-biphenyl axial chiral ligand according to claim 1, characterized in that,
the bisoxazoline ligand is a diastereoisomeric compound having configurations of (R) and (S) at the axis, and has the following formulae (II) and (III):

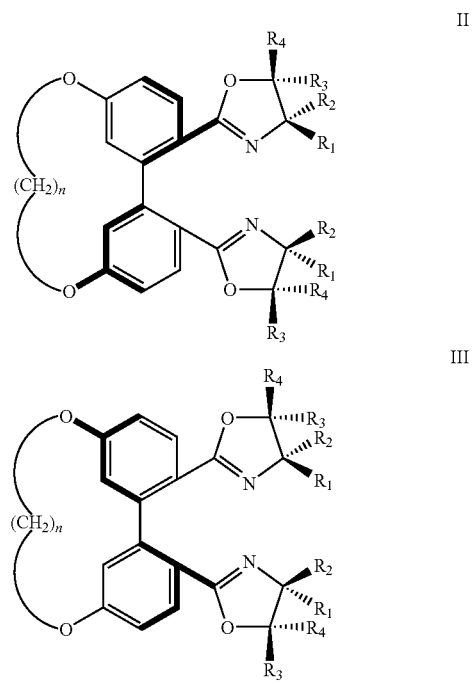

wherein: n5, 6, 7, 8, 9, 10, 11 or 12;
$R_1$=hydrogen, alkyl, substituted or unsubstituted aryl, substituted or unsubstituted benzyl;
$R_2$=hydrogen, alkyl, substituted or unsubstituted aryl, substituted or unsubstituted benzyl;
$R_3$=hydrogen, alkyl, substituted or unsubstituted aryl, substituted or unsubstituted benzyl;
$R_4$=hydrogen, alkyl, substituted or unsubstituted aryl, substituted or unsubstituted benzyl.

3. A method for preparing 5,5'-position linked 1,1'-biphenyl axial chiral ligands, characterized in that,
said method is a method for preparing 5,5'-position linked 1,1'-biphenyl axial chiral ligands of claim 1 comprising:
reacting a compound of formula (IX) with an activator that can activate the hydroxyl groups selected from the group consisting of an alkyl halosulfonium compound, an aryl halosulfonium compound, phosphorus oxychloride, phosphoryl chloride, phosphorus pentachloride, thionyl chloride and triphenyl phosphine, in the presence of alkali(s), with a dihalo alkane, to give a mixture of 5,5'-linked compounds of formulae (VIII) having configurations of (R) and (S) at the axis,

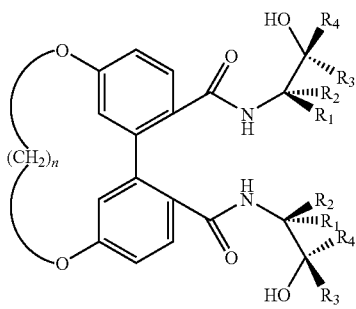

wherein n, $R_1$, $R_2$, $R_3$ and $R_4$ are as defined in claim 1.

4. A method for preparing 5,5'-position linked 1,1'-biphenyl axial chiral ligands, characterized in that, said method is a method for preparing 5,5'-position linked 1,1'-biphenyl axial chiral ligands of formulae (II) and (III) having configurations of (R) and (S) at the axis,

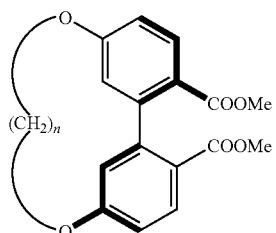

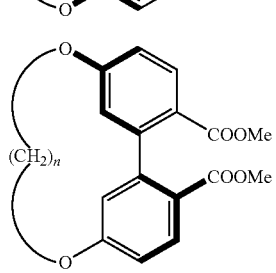

then reacting the compounds of formulae (VIII) with a chiral amino alcohol, to give amide compounds of formulae (IX) below having configurations of (R) and (S) at the axis,

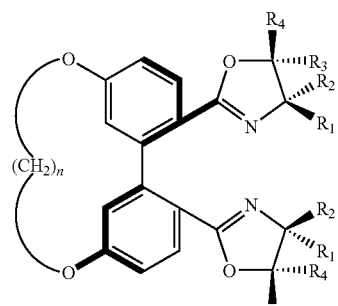

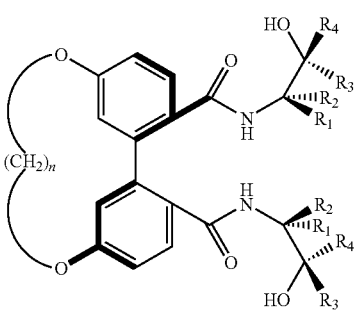

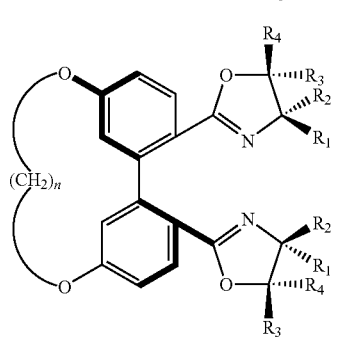

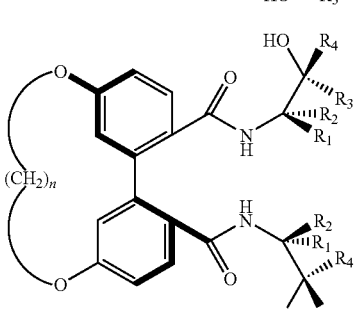

comprising:
reacting the compound of formula (VII),

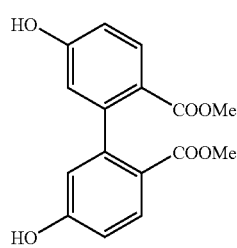

then reacting the amide compounds of formulae (IX) with an activator that can activate the hydroxyl groups selected from the group consisting of an alkyl halosulfonium compound, an aryl halosulfonium compound, phosphorus oxychloride, phosphoryl chloride, phosphorus pentachloride, thionyl chloride and triphenyl phosphine, in the presence of alkali(s) wherein in the above formulae, n, $R_1$, $R_2$, $R_3$ and $R_4$ are as defined in claim 1.

5. A method for preparing 5,5'-position linked 1,1'-biphenyl axial chiral ligands of formulae (II) and (III) having configurations of (R) and (S) at the axis, characterized in that, 2-bromo-4-methoxy benzophenone is used as a starting material and undergoes oxidation and esterification to give the compound of formula (V), the compound of formula (V) is then coupled through copper powder and undergoes a demethylation reaction to give methyl 5,5'-dihydroxy-1,1'-biphenyl-2,2'-dicarboxylate of formula (VII), then the compound of formula (VII) reacts with a dihalo alkane to give a mixture of 5,5'-linked compounds of formulae (VIII) having configurations of (R) and (S) at the axis, the compounds of formulae (VIII) then react with a chiral amino alcohol to give amide compounds of formulae (IX) having configurations of (R) and (S) at the axis, then the compounds of formulae (IX) react with an activator that can activate the hydroxyl groups selected from the group consisting of an alkyl halosulfonium compound, an aryl halosulfonium compound, phosphorus oxychloride, phosphoryl chloride, phosphorus pentachloride, thionyl chloride and triphenyl phosphine, in the presence of alkali(s) to give the target ligands of formulae (II) and (III) having configurations of (R) and (S) at the axis:

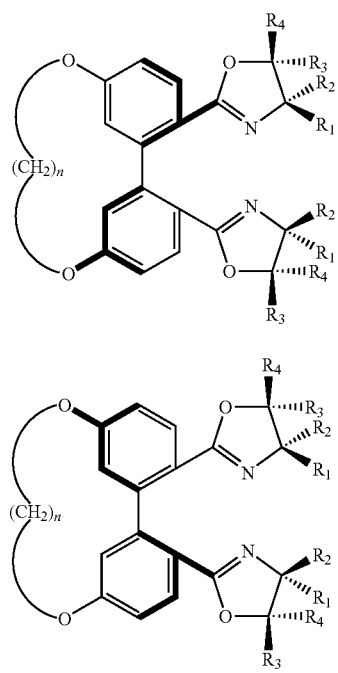

where the compounds of formulae (V) and (VII) have the formulae as follows:

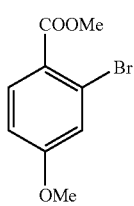

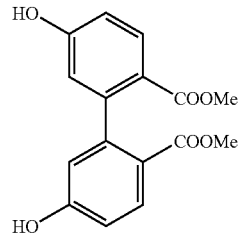

and where the compounds of formulae (VIII) and (IX) having a configuration of (R) at the axis have the formulae as follows:

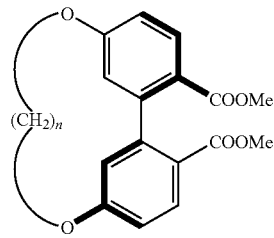

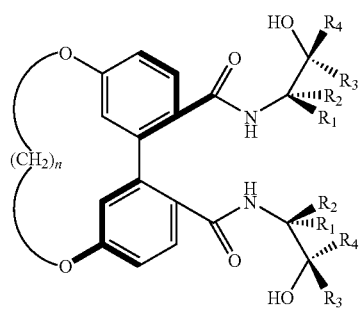

and where the compounds of formulae (VIII) and (IX) having a configuration of (S) at the axis have the formulae as follows:

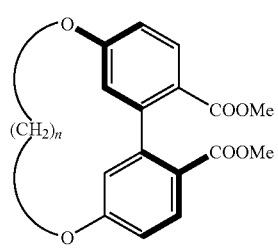

15

-continued

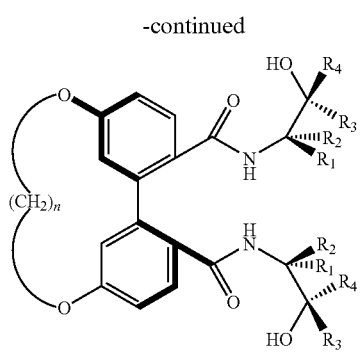

IX and where in the above formulae, n, $R_1$, $R_2$, $R_3$ and $R_4$ are as defined in claim 1.

6. The method for preparing 5,5'-position linked 1,1'-biphenyl axial chiral ligands of formulae (II) and (III) having configurations of (R) and (S) at the axis according to claim 5, characterized by comprising the following steps:

(1) 2-bromo-4-methoxy benzophenone is converted into 2-bromo-4-methoxy benzoic acid of formula (IV) in an aqueous solution with bromine added where the molar ratio of the 2-bromo-4-methoxy benzophenone to the bromine is 1:4-6;

(2) in an alcohol solvent and in the presence of thionyl chloride, the compound of formula (IV) is converted into methyl 2-bromo-4-methoxy benzoate of formula (V) where the molar ratio of the compound of formula (IV) to the thionyl chloride is 1:1-10;

(3) in the presence of copper powder, the compound of formula (V) is converted into methyl 5,5'-dimethoxy-1,1'-biphenyl-2,2'-dicarboxylate of formula (VI) where the molar ratio of the compound of formula (V) to the copper powder is 1:2-5;

(4) in an organic solvent and in the presence of ethanethiol, the compound of formula (VI) is reacted with aluminum trichloride to give methyl 5,5'-dihydroxy-1,1'-biphenyl-2,2'-dicarboxylate of formula (VII) where the molar ratio of the compound of formula (VI) to the aluminum trichloride is 1:3-6;

(5) in organic solvent(s), methyl 5,5'-dihydroxy-1,1'-biphenyl-2,2'-dicarboxylate of formula (VII) is reacted with a dihalo alkane in the presence of alkali(s) to prepare a mixture of 5,5'-linked compounds of formulae (VIII) having configurations of (R) and (S) at the axis where the molar ratio of the methyl 5,5'-dihydroxy-1,1'-biphenyl-2,2'-dicarboxylate of formula (VII) to the dihalo alkane is 1:1-1.5;

(6) the mixture of compounds of formulae (VIII) having configurations of (R) and (S) at the axis is reacted with a chiral amino alcohol in the presence of alkali(s), to give amide diastereoisomeric compounds of formulae (IX) having configurations of (R) and (S), respectively, at the axis where the molar ratio of the mixture of compounds of formulae (VIII) to the chiral amino alcohol is 1:3-10;

(7) in organic solvent(s) and in the presence of alkali(s) and an activator that can activate the hydroxyl groups selected from the group consisting of an alkyl halosulfonium compound, an aryl halosulfonium compound, phosphorus oxychloride, phosphoryl chloride, phosphorus pentachloride, thionyl chloride and triphenyl phosphine, amide diastereoisomeric compounds of formulae (IX) having configurations of (R) and (S) at the axis are converted into compounds of formulae (II) and (III)

16 having configurations of (R) and (S), respectively, at the axis where the molar ratio of the amide compounds of formulae (IX) having configurations of (R) and (S) at the axis to the alkali to the activator is 1:5-25:3-12, where the compounds of formulae (IV) and (VI) have the formulae as follows:

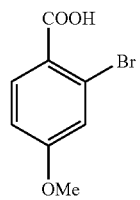

IV

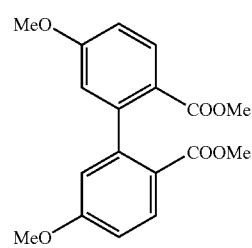

VI and where the compounds of formulae (II) and (III) having a configuration of (R) and (S) at the axis have the formulae as follows:

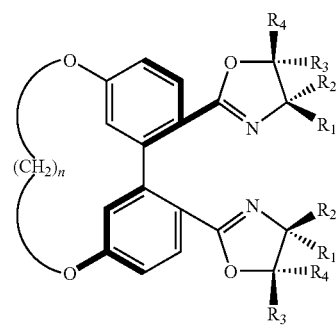

II

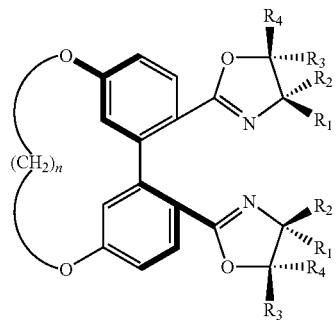

III and where in the above formulae, n, $R_1$, $R_2$, $R_3$ and $R_4$ are as defined in claim 5 and where the compounds of formulae (V) and (VII), compounds of formulae (VIII) and (IX) having a configuration of (R) at the axis, and compounds of formulae (VIII) and (IX) having a configuration of (S) at the axis have the formulae as defined in claim 5.

7. The method for preparing 5,5'-position linked 1,1'-biphenyl axial chiral ligands of formulae (II) and (III) having configurations of (R) and (S) at the axis according to claim 6, characterized in that, in the step (1), the concentration of the aqueous sodium hydroxide is 5-20 wt %, the reaction temperature is 20-70° C., and the reaction time is 12-20 hrs.

8. The method for preparing 5,5'-position linked 1,1'-biphenyl axial chiral ligands of formulae (II) and (III) having configurations of (R) and (S) at the axis according to claim 6, characterized in that, in the step (2), the reaction temperature is 20-80° C., and the reaction time is 1-12 hrs.

9. The method for preparing 5,5'-position linked 1,1'-biphenyl axial chiral ligands of formulae (II) and (III) having configurations of (R) and (S) at the axis according to claim 6, characterized in that, in the step (3), the reaction temperature is 150-180° C., and the reaction time is 2-24 hrs.

10. The method for preparing 5,5'-position linked 1,1'-biphenyl axial chiral ligands of formulae (II) and (III) having configurations of (R) and (S) at the axis according to claim 6, characterized in that, in the step (4), the reaction temperature is 0-25° C., and the reaction time is 2-6 hrs.

11. The method for preparing 5,5'-position linked 1,1'-biphenyl axial chiral ligands of formulae (II) and (III) having configurations of (R) and (S) at the axis according to claim 6, characterized in that, in the step (5), the reaction temperature is 20-100° C., the reaction time 8-72 hrs, the dihalo alkane is

wherein m=3, 4, 5, 6, 7, 8, 9 or 10; and X and X' are chloride, bromide or iodide.

12. The method for preparing 5,5'-position linked 1,1'-biphenyl axial chiral ligands of formulae (II) and (III) having configurations of (R) and (S) at the axis according to claim 6, characterized in that, in the step (6), the reaction temperature is 50-120° C., and the reaction time is 4-12 hrs.

13. The method for preparing 5,5'-position linked 1,1'-biphenyl axial chiral ligands of formulae (II) and (III) having configurations of (R) and (S) at the axis according to claim 6, characterized in that, in the step (7), the reaction temperature is room temperature, and the reaction time is 12-36 hrs.

* * * * *